United States Patent [19]
Rodriguez

[11] Patent Number: 5,863,529
[45] Date of Patent: Jan. 26, 1999

[54] SUPPRESSION OF DEMYELINATION BY INTERLEUKIN-6

[75] Inventor: Moses Rodriguez, Rochester, Minn.

[73] Assignee: Mayo Foundation for Medical Education and Research, Rochester, Minn.

[21] Appl. No.: 530,654

[22] Filed: Sep. 20, 1995

[51] Int. Cl.$^6$ .................................................. A61K 38/20
[52] U.S. Cl. ................................ 424/85.2; 514/12; 514/2
[58] Field of Search .......................... 514/2, 12; 424/85.2

[56] References Cited

U.S. PATENT DOCUMENTS 5,437,863  8/1995  Williams et al. ...................... 424/85.1

OTHER PUBLICATIONS

Savino et al. Proc. Natl. Acad. Sci USA 90 (1993) 4067–4071.
Ehlers et al. Annals New York Acad. Sci. 762(1995) 400–402.
Li et al. J. of Biological Chemistry 268 (1993) 22377–22384.
Lee Beek et al. J. of Biological Chemistry 267 (1992) 14832–14838.
Hammacher et al. Protein Science 3 (1994) 2280–2293.
Fontaine et al. Eur. J. Biochem. 211 (1993) 749–755.
Rodriguez et al. J. Immunol. 153 (1994) 3811–3812.
Cohen. Science 270 (1995) 908.
Desquenne –Clark et al. PNAS 88 (1991) 7219–7223.
Osband et al. Immunology Today 11 (1990) 193–195.
Rudinger. In "Peptide Hormones", ed. J.A Parsons (Jun. 1976) University Park Press, Baltimore, pp. 1–7.
Porrini et al. Cell Immunol. 157 (1994) 428–438.
Dal Canto et al. *Ann. Neurol* 11:109 (1982).
Compston, A. and Sadovnick, A.D., *Curr. Opin. Neurol. Neurosurg.* 5:175 (1992).
Akira, et al., *IL–6 and NF–IL6 in Acute–Phase Response and Viral Infection,* Immunological Reviews, No. 127, pp.25–50 (1992)
Carter, et al., *The Immunopathology of Multiple Sclerosis,* Current Opinion in Neurology and Neurosurgery, 4:186–190 (1991).
Frei, et al., *Interleukin–6 is Elevated in Plasma in Multiple Sclerosis,* Joural of Neuroimmunology 31:147–153 (1991).
Frei, et al., *On the Cellular Source and Junction of Interleukin–6 Produced in the Central Nervous System in Viral Diseases,* Eur. J. Immunol., 19:689–694 (1989)
Gijbels, et al., *Interleukin 6 Production in the Central Nervous System During Experimental Autoimmune Encephalomyelitis,* Eur. J. Immunol., 20:233–235 (1990).

Henke, et al., *Coxsackievirus B3–Induced Production of Tumor Necrosis Factor–α, IL–1β, and IL–6 in Human Monocytes,* The Journal of Immunology, vol. 148, 2270–2277, No. 7, Apr. 1, 1992.
Joseph, et al., *Interleukin–6 Induction in Vitro in Mouse Brain Endothelial Cells and Astrocytes by Exposure to Mouse Hepatitis Virus (MHV–4, JHM),*Journal of Neuroimmunology, 42:47–52 (1993).
Maimone, et al., *Norepinephrine and Vasoactive Intestinal peptide Induce IL—6 Secretion by Astrocytes: Synergism With IL–1β and TNFα,* Journal of Neuroimmunology, 47:73–82 (1993).
Patick, et al., *Major Histocompatability Complex–Conferred Resistance to Theiler's Virus–Induced Demyelinating Disease is Inherited as a Dominant Trait in B10 Congenic Mice,* J. of Virology, 64:5570–76(1990).
Paya, et al., *Inhibition of Theiler's Virus–Induced Demyelination in vivo by Tumor Necrosis Factor Alpha,* International Immunology, vol. 2, No. 9, pp. 909–913 (1990).
Rodriguez, Moses, *Multiple Sclerosis: Basic Concepts and Hypothesis,* Mayo Clin. Proc, 64:570–6 (1989).
Rodriguez, Moses,*Mechanisms of Virus–Induced Demyelination and Remyelination$^α$,* Advances in Neuroimmunology, vol. 540 of the Annals of the New York Academy of Sciences,pp. 240–251 (Nov. 28, 1988).
Rodriguez, et al., *Role of T Cell Receptor Vβ Genes in Theiler's Virus–Induced Demyelination of Mice,* The Journal of Immunology, 148:921–927 (1992).
Rodriguez, et al., *Theiler'Murine Encephalomyelitis: A Model of Demyelination and Persistence of Virus,* CRC Critical Reviews in Immunology, vol. 7, Issue 4, pp. 325–365 (1987).
Rodriguez, et al., *Expression of Human HLA–B27 Transgene Alters Sussceptibility to Murine Theiler's Virus–Induced Demyelination,* The Journal of Immunology, 146:2596–2602 (1991).
Sëbire, et al.,*In Vitro Production of IL–6, IL–1β, and Tumor Necrosis Factor–α by Human Embryonic Microglial and Neural Cells,* The Journal of Immunology, 150:1517–1523 (1993).

Primary Examiner—Paula K. Hutzell
Assistant Examiner—Robert C. Hayes
Attorney, Agent, or Firm—Fish & Richardson P.C., P.A.

[57] ABSTRACT

A method of suppressing demyelination of the central nervous system is disclosed. The method comprises administering a therapeutically effective amount of Interleukin-6 or an analog thereof to a mammal. Methods of treating multiple sclerosis and a related article of manufacture are also disclosed.

7 Claims, 4 Drawing Sheets

DEMYELINATION AND VIRUS-ANTIGEN CORRELATION

Fig. 4

VIRUS TITERS IN rIL6-TREATED MICE

SUPPRESSION OF DEMYELINATION BY INTERLEUKIN-6

BACKGROUND OF THE INVENTION

Multiple Sclerosis (MS) is a progressive, immune-mediated primary demyelinating disease of the central nervous system (CNS). Primary demyelination is the pathologic process characterized by the destruction of myelin sheaths with relative maintenance of axons and other neuronal structures. MS is the principal human CNS primary demyelinating disease, although there are other rare forms of demyelinating disease that affect the brain and spinal cord, including Schilder's disease, Balos concentric sclerosis, acute disseminated encephalomyelitis, acute hemorrhagic leukoencephalopathy, tropical spastic paraparesis, and human T-cell leukemia virus (HTLV)-I-associated myelopathy.

MS affects scattered areas of the CNS with a predilection for periventricular white matter, brainstem, spinal cord, and optic nerves. The CNS plaques associated with MS are characterized by primary demyelination and death of oligodendrocytes (myelin-producing cells) within the center of the lesion. During the early evolution of the plaque, perivascular inflammatory cells (lymphocytes, plasma cells, macrophages) invade the substance of the white matter and are thought to play a critical role in myelin destruction. This process is followed by extensive gliosis by astrocytes and aberrant attempts at remyelination with oligodendrocytes proliferating at the edges of the plaque. In addition, immunoglobulins are deposited with each plaque.

Although the etiology and pathogenesis of MS is unknown, epidemiologic studies indicate that clinical exacerbations of the disease may be triggered by a virus. Under this hypothesis, the destruction of myelin or oligodendrocytes may result from an immune attack directed against self or against novel antigen plus self, which is triggered by the virus. See Rodriguez, *Multiple Sclerosis: basic concepts and hypothesis*, Mayo Clin. Proc., 64:570–6 (1989).

Viruses from many families and subfamilies (Herpetoviridae, Coronaviridae, Picornaviridae, Lentiviridae, Paramyxoviridae, Togaviridae) experimentally induce demyelination in animals of various species (e.g., mice, rats, dogs, sheep). Dal Canto et al., Ann. Neurol., 11:109 (1982). Epidemiologic studies based on migration data and differences in prevalence rates in various parts of the world indicate that MS is triggered by an exogenous factor such as a virus. Compston et al., Epidemiology and genetics of multiple sclerosis; Curr. Opin. Neurol. Neurosurg., 5:175 (1992). The low rate of concordance (20–30%) in monozygotic twins in which one has MS suggests that an exogenous factor, possibly a virus, as well as host genetics, plays a role in pathogenesis of the proposed animal models of CNS demyelination, Theiler's murine encephalomyelitis (TME) has received wide attention. Infection of susceptible strains of mice, (SJL/J), prototypic strain, with Theiler's murine encephalomyelitis virus (TMEV) results in virus persistence and chronic primary immune-mediated demyelination. Intracerebral infection with TMEV results in acute encephalitis, characterized by viral replication in neurons and inflammation in the brain. This acute infection is followed by a progressive primary demyelinating disease of the spinal cord (beginning 10 to 14 days after infection), characterized by viral persistence in macrophages, astrocytes, and oligodendrocytes. Studies of this model system have shown that chronic infection with TMEV results in demyelinating disease that has many similarities to MS.

As in MS, during the chronic phase of TMEV infection, the pathological abnormalities are limited to the CNS. The histological appearance is characterized by primary demyelination. In addition, as in the human disease, inflammatory cells and macrophages are intimately involved in the demyelinating process. After a long incubation period, this results in spasticity, weakness of the lower extremities, and bladder incontinence. The pathological change in the spinal cord is also characterized by recurrent episodes of acute demyelination superimposed on a chronic progressive disease that mimics the exacerbations and remissions observed clinically in the human disease. See, Rodriguez et al., *Theiler's murine encephalomyelitis: A model of demyelination and persistence of virus*, Crit. Rev. Immunol., 7:325 (1987). The TMEV murine model has provided an excellent way to test various therapeutic modalities to prevent or inhibit demyelination. Immunosuppression by using cyclophosphamide, antilymphocyte serum, cyclosporin, monoclonal antibodies (mAbs) to immune-response gene products (I-A), and mAbs to CD4 or CD8 has been shown to diminish the extent of demyelinating disease.

Administration of recombinant human or mouse tumor necrosis factor alpha (TNF-α) inhibits TMBV-induced demyelination in susceptible SJL/J mice without affecting virus replication in the CNS. TNF-α is also made by some activated T cells. Paya et al., Int'l Immunol., 2:909 (1990). These studies indicate that manipulation of the immune response by using pharmacologic agents, mAbs, or recombinant biologic products may influence the extent of demyelinating disease.

Recently, the role of interleukin-6 (IL-6) in the pathogenesis of inflammatory diseases of the CNS, including viral infections and MS, has been investigated. IL-6 is a cytokine of approximately 26 kD that is synthesized by mononuclear phagocytes, vascular endothelial cells, fibroblasts, and other cells in response to IL-1 and, to a lesser extent, TNF. IL-6 is one of the major mediators of the immune response, with pleiotropic effects on many different target cells. Along with TNF-α, IL-1, and IFN γ, IL-6 belongs to a family of endogenous mediators in the reaction of the host to injury or infection referred to as the acute phase response. Astrocytes produce IL-6, and IL-1β and TNF-α provide a strong inducing signal for IL-6 production. IL-6 mRNA and IL-6 receptor mRNA have been localized by in situ hybridization to neurons and astrocytes of rat brain. Astrocyte-produced IL-6 has been proposed to play a role in augmenting intracerebral immune responses. Increased levels of IL-6 have been detected in the CNS of mice suffering from the lethal forms of experimental autoimmune encephalomyelitis, an autoimmune model of MS. Gijbels et al., Eur. J. Immunol., 20:233 (1990). Neurotrophic viruses, such as Newcastle disease virus, trigger IL-6 as well as TNF-α, IFN-α, and TFN-β production by astrocytes. Laboratory viruses Sendai, Mengo, and Newcastle disease virus stimulate IL-6 production in fibroblasts in a dose dependent manner. Infection of human skin fibroblasts in culture by dengue virus results in the production of IL-6, as well as IFN-9 and granulocyte-macrophage-CSF. Increased transcription of IL-6 has been detected in the brain of mice with chronic coxsackie B1 virus infection. IL-6 is produced in vitro in mouse brain endothelial cells and astrocytes after infection with the demyelinating variant of mouse hepatitis virus, a Coronavirus. Joseph et al., J. Neuroimmunol., 42:47 (1993). IL-6 is produced in the CNS of mice infected with lymphocytic choriomeningitis virus (LCMV) and vesicular stomatitis virus. In vitro assays demonstrate that microglia and astrocytes infected by LCMV secrete IL-6, suggesting that IL-6 may be involved in repair mechanisms initiated in the course of viral-induced CNS damage. Frei et al., Eur. J. Immunol., 19:689 (1989).

IL-6 has been implicated in the pathogenesis of human inflammatory CNS diseases. Increased plasma and cerebrospinal fluid levels of IL-6 have been demonstrated in patients with MS (Frei et al., J. Neuroimmunol., 31:147 (1991)), HTLVI-associated myelopathy, and bacterial meningitis. Elevated levels of IL-6 have been detected in the cerebrospinal fluid of patients with CNS involvement from systemic lupus erythematosus and systemic vasculitides. Patients infected with HIV-1 produce elevated levels of IL-6, IL1, and TNF-α, raising the possibility that these cytokines play a role in AIDS nervous system disease.

Although IL-6 has been implicated in viral-induced damage repair mechanisms, a role for IL-6 in therapeutic suppression of CNS demyelination in disorders such as MS has not been postulated. Clearly, it would be desirable to identify any factor that suppresses CNS demyelination, and any such factor would thus be a candidate for treatment of MS and other CNS demyelination disorders.

SUMMARY OF THE INVENTION

In one aspect, the present invention features a method of suppressing demyelination of central nervous system tissue. The method comprises the step of administering a therapeutically effective amount of interleukin-6 (IL-6) or an analog thereof to a mammal.

Preferably, the IL-6 is recombinant human IL-6 (rIL-6). In other preferred embodiments, the invention may comprise administering an analog of IL-6 derived from rIL-6, or a synthetic peptide analog of IL-6, wherein the analog has the demyelination suppression activity of IL-6.

The therapeutically effective amount of IL-6 or IL-6 analog may be administered enterally or parenterally. Preferably, the IL-6 or analog thereof is administered subcutaneously.

In another aspect, the present invention features a method of treatment of multiple sclerosis. This method comprises the step of administering a therapeutically effective amount of interleukin-6 or an analog thereof to a patient who has been diagnosed with, or who is suspected of acquiring, multiple sclerosis.

Finally, the invention features an article of manufacture having packaging material and a pharmaceutical agent contained within the packaging material. The pharmaceutical agent is therapeutically effective for suppressing demyelination of central nervous system tissue. The packaging material contains a label indicating that the pharmaceutical agent can be used for suppressing demyelination of central nervous system tissue. The pharmaceutical agent comprises IL-6 or an analog thereof.

DETAILED DESCRIPTION OF THE INVENTION

The present invention covers a method of suppressing demyelination of the CNS by administering a therapeutically effective amount of interleukin-6 or an analog thereof to a mammal.

Experiments in mice, described below, demonstrate that in vivo administration of recombinant human IL-6 (rIL-6) diminishes the extent of myelin destruction in a viral model of MS. The viral model utilized here, TMEV-induced demyelinating disease in SJL/J mice, is known to be an excellent model for MS and for testing potential therapeutic modalities for MS.

In particular, rIL-6 had a therapeutic effect when treatment was begun 15 days after intracerebral infection with TMEV. This finding is significant because the time for initiating treatment in these experiments was chosen to simulate the human situation in which therapy is begun at the onset of the first apparent clinical deficit.

Although the mechanism by which rIL-6 treatment diminishes the extent of myelin destruction in the TMEV model system is not known, it is significant that, as shown below, treatment with rIL-6 diminished the number of virus antigen (Ag)-positive cells in the spinal cord of chronically infected SJL/J mice. Previous studies using recombinant inbred strains of mice have documented excellent correlation between viral Ag production in the spinal cord and the extent of demyelinating disease. Rodriguez et al., J. Immunol., 146:2596 (1991); Patrick et al., J. Virol., 64:5570 (1990); Rodriguez et al., J. Immunol., 148:921 (1992). It is possible, therefore, that rIL-6 diminishes demyelination by inhibiting replication of virus and limiting virus Ag production in the spinal cord. It is also possible that rIL-6 may have worked in conjunction with other lymphokines and cytokines in vivo to inhibit virus replication in the spinal cord. IL-1, TNF-α, IFN-γ, and IL-6 are known to play a synergistic role in the acute phase reaction to injury. Akira et al., Immunol. Rev., 127:25 (1992); Sebire et al., J. Immunol., 150:1517 (1993); Henke et al., J. Immunol., 148:2270 (1992); Maimone et al., J. Neuroimmunol., 47:73 (1993). These lymphokines and cytokines may work in concert during the acute phase of TMEV-induced disease to suppress demyelination. Other possible mechanisms include a rIL-6-induced protective class I-restricted immune response or a direct, IL-6 mediated anti-inflammatory effect.

Irrespective of the possible mechanisms of action, the present invention exploits the heretofore undiscovered suppressive effect of IL-6 on virus-induced demyelination of the CNS as a therapeutic method of suppressing demyelination of the CNS. The murine, TMEV-induced demyelination model employed herein is documented as an excellent animal model for human MS. The demyelinating disease produced by chronic TMEV invention has many similarities to MS, and the model is particularly attractive because of the suggestion by many investigators that MS results from an immune-mediated response triggered by virus infection in the nervous system.

In the Examples below, the animal model and conditions of infection and therapy all are selected to simulate the disease of multiple sclerosis in humans (and other CNS demyelination diseases), and some of the Examples are designed to simulate the typical human situation of initiating therapy at the onset of the first apparent clinical deficit, while others simulate presymptomatic initiation of therapy.

Accordingly, the present invention relates in one aspect to a method of suppressing demyelination of the CNS. The suppression of demyelination of the CNS may be achieved in at least three ways in terms of the timing of initiation of IL-6 therapy.

First, and most common, suppression of CNS demyelination is achieved by initiation of IL-6 therapy at the onset of the first apparent clinical deficit, e.g., visual blurring, numbness, weakness, fatigue, bladder incontinence, sexual dysfunction, or any other symptom related to CNS demyelination. This treatment modality is illustrated and described in the Examples below in the TMEV model system.

Two other treatment modalities involve presymptomatic initiation of IL-6 therapy. First, if it is the case (as is suspected) that an exogenous agent, such as a virus, triggers demyelination of the CNS, then it would be possible to detect the presence of the exogenous agent in the host and initiate IL-6 treatment upon confirmation of infection, but before the onset of clinical deficit. This treatment modality is illustrated in the Examples below. Second, if it is the case that host genetics play a role in the etiology and pathogenesis of CNS demyelination, it may be possible to ascertain genetic predisposition to CNS demyelination disorders and initiate IL-6 treatment prior to the onset of clinical deficit.

Each of the above-described treatment modalities for suppressing CNS demyelination is within the scope of the present invention.

Thus, the present invention covers the use of IL-6 therapy to suppress demyelination at any time prior to or during the course of the demyelination disorder.

The method of suppressing CNS demyelination of the present invention involves administering a therapeutically effective amount of IL-6 or an analog thereof.

The suppression of demyelination of CNS tissue (i.e., brain and spinal cord) with IL-6 or analog thereof may be achieved by any method of delivery of a therapeutant known in the art. In preferred embodiments of the invention, IL-6 or analog thereof is administered parenterally by subcutaneous injection in a buffered saline solution or other suitable carrier. The IL-6 or analog thereof may be administered enterally or parenterally.

By "IL-6 or an analog thereof", it is intended that the present invention cover the administration (1) of the whole IL-6 cytokine molecule, including recombinant human IL-6, as described in the Examples below, and (2) of an analog of IL-6. Analogs of IL-6 include (1) fragments of IL-6 or rIL-6, (2) IL-6 or rIL-6 having conservative amino acid changes, (3) synthetic peptides, and (4) chemically modified IL-6, rIL-6 or fragments thereof, such as those containing additional material functioning as carrier sequences to prevent degradation of the therapeutically effective portion, all of which are substantially homologous with or correspond to the sequence of native human IL-6. IL-6 analogs appropriate for use in the present invention have the demyelination suppression activity of IL-6.

It is possible to ascertain the portion of the IL-6 molecule (i.e., an analog) responsible for the suppression of demyelination. This involves testing the efficacy of fragments of various sizes from various regions of the IL-6 molecule using the experimental models described in the Examples below. Once a candidate analog is identified which functions to suppress demyelination, this analog is used as a therapeutant for CNS demyelination. In the case of IL-6 fragments, the relatively smaller size of an efficacious IL-6 analog could provide a number of advantages, including lower cost and easier handling.

In preferred embodiments of the present invention, recombinant human IL-6 (rIL-6) is used in the step of administering a therapeutically effective amount of IL-6. rIL-6 is obtainable as a recombinant expression product of E. coli., Asagoe et al., Biotechnology, 6:806 (1988). In other embodiments, analogs of IL-6, as contemplated by the present invention and described above, can be derived from rIL-6 or synthesized using peptide synthesis techniques known in the art.

A therapeutically effective amount of IL-6 or analog thereof for treatment of a human patient may be determined by means known to those of ordinary skill in the art. For example, an effective dosage for humans may be extrapolated from the 5.0 $\mu$g/day shown below to be therapeutically effective in mice, provided such an extrapolated dosage is determined to be clinically efficacious.

Other demyelination disorders of the CNS are known, as described above. It is intended that the present invention cover a method of suppressing demyelination in any of the known CNS demyelination disorders.

In a preferred embodiment, the invention relates to a method of treating multiple sclerosis (MS). In this embodiment, the CNS tissue of a therapeutically effective amount of IL-6 or an analog thereof is administered to a patient who is diagnosed with MS (by any means of diagnosis known in the art) or who is suspected of acquiring (i.e. because of a viral infection or because of genetic predisposition as described above).

In an alternative embodiment, the present invention relates to an article of manufacture having packaging material and a pharmaceutical agent contained within the packaging material. The pharmaceutical agent is therapeutically effective for suppressing demyelination of central nervous system tissue. The packaging material contains a label indicating that the pharmaceutical agent can be used for suppressing demyelination of central nervous system tissue. The pharmaceutical agent comprises IL-6 or an analog thereof, as defined above.

EXAMPLE I rIL-6 suppression of TMEV-induced demyelination

Materials and Methods. SJL/J mice were obtained from The Jackson Laboratories (Bar Harbor, Me.) and used for experiments after a 1-week rest. Female mice at 4–8 weeks of age were injected intracerebrally with $2\times10^5$ PFU of virus in a 10 $\mu$l volume.

Human rIL-6 was expressed in E. coli and purified (Asagoe et al., Biotechnology, 6:806 (1988)), and provided by Chugai Pharmaceutical Co., Ltd., Shizyoka, Japan. rIL-6 was administered subcutaneously in the back of mice at a dose of 2.5 $\mu$l (5 $\mu$l/day) beginning 1 day before infection (day −1). rIL-6 was dissolved in PBS containing 10% normal mouse serum (NMS). All control animals received the diluent containing PBS/10% NMS without IL-6.

Mice were killed for pathologic analysis on day 28. Mice were anesthetized with 0.2 mL of pentobarbital (i.p.) and perfused by intracardiac puncture with Trump's fixative. Rodriguez et al., Neurology, 36:964 (1986). Spinal cords were removed and sectioned coronally into 30 to 35 blocks (1–2 mm thick) from each mouse, as described in: Id.; Rodriguez et al., *Microb. Pathog.*, 11:269 (1991); Rodriguez et al., *J. Immunol.*, 146:2596 (1991). Every third spinal cord block was embedded in glycol-methacrylate plastic, and 1-$\mu$ sections were stained with an erichrome stain for myelin on osmicated tissue. Pierce et al., *V. Histotechnol.* 12:35 (1989). The remaining of the blocks were stored in 0.1 m phosphate buffer for frozen sections. Detailed morphologic analysis was performed on the plastic-embedded sections by examining for the presence of gray matter inflammation, meningeal inflammation, and demyelination in each quadrant from every spinal cord. Rodriguez et al., Neurology, 36:964 (1986); Rodriguez et al., Microb. Pathog., 11:269 (1991); Rodriguez et al., J. Immunol., 146:2596 (1991). This resulted in the analysis of 1106 spinal cord quadrants. A maximum score of 100 represented the presence of pathologic abnormalities in every quadrant from every spinal cord section from one mouse.

Results. Treatment with rIL-6 markedly diminished the extent and severity of demyelinating lesions in the spinal cord. In the six TMEV-infected SJL/J mice treated with PBS/10% NMS, an average of 38% of 342 spinal cord quadrants examined showed demyelination (Table 1).

Figure 2A:
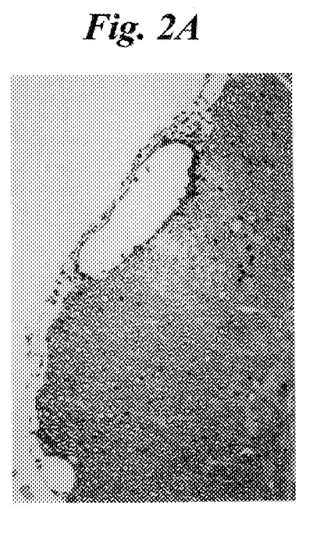
FIGS. 2A–2B show spinal cord sections of TMEV-infected mice treated with rIL-6 beginning at day (+15).
Figure 2B:
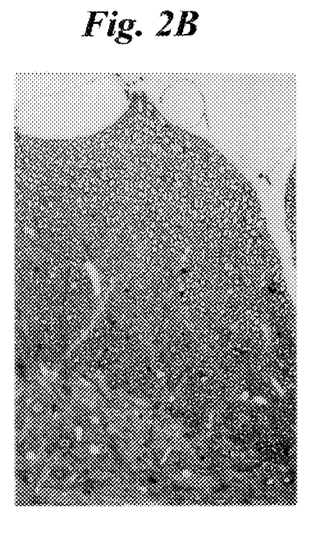

TMEV-infected SJL/J mice treated with rIL-6 (beginning on day +15), an average of 10% of 402 spinal cord quadrants examined showed demyelination (Table 1) compared with 39% of spinal cord quadrants in the controls. Similar to animals treated with rIL-6 beginning on day −1, most lesions showed small areas of inflammation and minimal demyelination (FIG. 2A), or no demyelination (FIG. 2B). This difference in demyelination scores between mice treated with rIL-6 (beginning on day +15) and control mice treated with PBS/10% NMS (beginning on day −1) was highly statistically significant (p=0.001).

EXAMPLE III

Association of Therapeutic Effect of IL-6 With Reduction of Virus Ag-Positive Cells in Spinal Cord Materials and Methods. Immunocytochemistry for virus Ag was performed in spinal cord sections. For immunoperoxidase studies, coronal spinal cord sections from perfused animals were stored in 0.1M phosphate buffer, rinsed in 0.1M Tris buffer with 35 mM hydroxylamine (pH 7.4), treated with 10% dimethyl sulfoxide for 1 hour, and quick

TABLE 1

Spinal cord pathology in TMEV-infected mice treated with human rIL-6.

| Treatment | n[a] | Protocol[b] | Pathology Score (mean ± SEM) | | | p[c] |
| --- | --- | --- | --- | --- | --- | --- |
| | | | Gray Matter Inflammation | Meningeal Inflammation | Demyelination | |
| rIL-6 | 7 | −1 | 0.0 ± 0.0 | 14.0 ± 5.4 | 13.6 ± 6.5 | |
| rIL-6 | 7 | +15 | 0.3 ± 0.2 | 9.5 ± 2.3 | 10.1 ± 2.2 | 0.02 |
| PBS/10% NMS | 6 | −1 | 0.3 ± 0.3 | 35.2 ± 7.9 | 38.7 ± 6.7 | 0.001 |

[a]n = Number of SJL/J mice
[b]Day of the start of twice daily treatment, where 0 is the day of virus infection.
[c]Statistics by Student's t-test comparing demyelination scores.

Figure 1A:
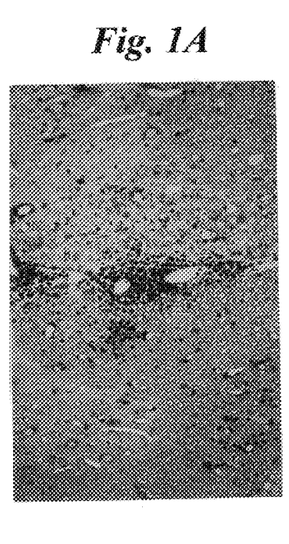
FIGS. 1A–1D show spinal cord sections of TMEV-infected mice treated (1C–1D) and not treated (1A–1B) with rIL-6, treatment beginning at day (−1).
Figure 1B:
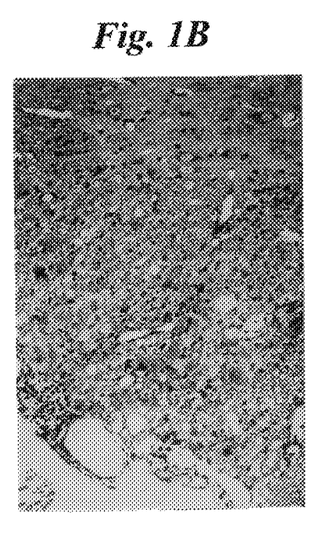
Figure 1C:
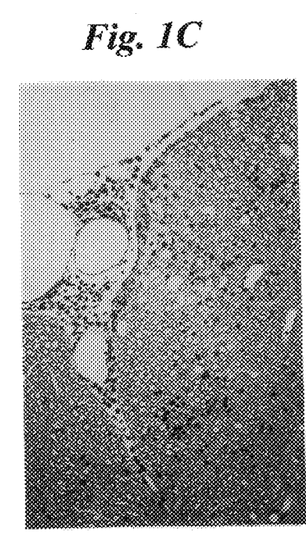
Figure 1D:
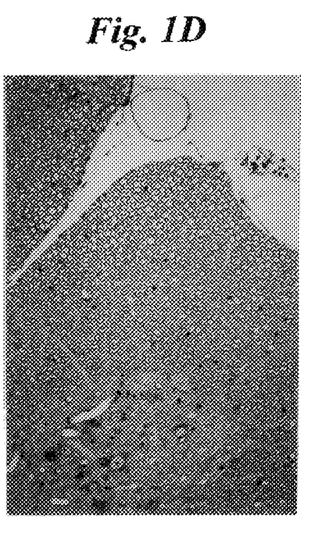

Many of these lesions were extensive, involving most of the spinal cord white matter (FIGS. 1A and 1B). There were multiple focal areas of perivascular inflammation (FIG. 1A) that were localized exclusively within the white matter. Many large plaques contained multiple demyelinated axons in association with macrophages (FIG. 1B). In contrast, in TMEV-infected SJL/J mice treated with IL-6 (beginning on day −1), an average of only 14% of the 362 spinal cord quadrants examined showed demyelination. This difference in demyelination scores comparing rIL-6 treated to control-treated mice was statistically significant (p=0.02). In mice treated with rIL-6, the pathologic abnormalities were much less prominent (FIGS. 1C and 1D). Focal areas of perivascular inflammation with only minimal demyelination were observed (FIG. 1C). Most spinal cord quadrants showed normally preserved myelinated axons without demyelination (FIG. 1D).

EXAMPLE II

Therapeutic Utility of IL-6

Materials and Methods. Therapeutic utility of IL-6 was determined by initiating twice daily treatment (as described above in Example I) on day +15, a time during which there is definite inflammation in the spinal cord in the murine TMEV model, but only early demyelination.

Results. This experimental paradigm was used to simulate the treatment of human MS at disease onset. In the seven frozen in isopentane chilled in liquid nitrogen. Pierce et al., *J. Histotechnol.*, 12:35 (1989). The avidin biotin immunoperoxidase system was performed on 10-$\mu$ crystal sections by using polyclonal rabbit-antiserum to purified TMEV Daniel's strain virions. Rodriguez et al., *Ann. Neurol.*, 13:426 (1983). This polyclonal antiserum specifically reacts to all structural proteins of TMEV. Id.

For quantitative analysis of a number of virus Ag-positive cells, five to six spinal cord-coronal sections from each mouse were processed for immunocytochemistry. A Zeiss microscope with a camera lucida attachment was used to project the spinal cord images onto a ZIDAS (Carl Zeiss Inc., Oberkochen, Germany) digitizing tablet. Spinal cord areas were traced to determine total area (mm$^2$). A minimum of 1.10 mm$^2$ to a maximum of 6.865 mm$^2$ of spinal cord was examined for each mouse. The number of virus Ag-positive cells for each mouse was counted and expressed per area of spinal cord. This allowed correlation of the number of virus Ag-positive cells with the extent of demyelination.

The association of the therapeutic effect observed with rIL-6 treatment with the reduction of virus Ag-positive cells in the spinal cord was examined. Previous studies have indicated excellent correlation between the number of virus Ag-positive or virus RNA-positive cells, and the extent of demyelination. Five to six spinal cord blocks from animals treated with rIL-6 (beginning on day −1), rIL-6 (beginning on day +15), and PBS/10% NMS (beginning on day −1)

were embedded for frozen sections and stained for virus Ags by using the avidin-biotin immunoperoxidase technique. Virus Ag-positive cells were identified easily by their brown reaction product with use of the Hanker-Yates detection reagent. The number of virus Ag-positive cells per total area of spinal cord was determined by using morphometric techniques. The total area of spinal cord analyzed (on average 3.6 to 4.0 mm$^2$) was similar in the three treatment groups (Table 2).

TABLE 2

Spinal cord pathology in TMEV-infected mice treated with human rIL-6.

| Treatment | n[a] | Pro-tocol[b] | Ag-Positive[c] Cells (No.) | Spinal Cord Area (mm$^2$)[c] | Cells per[c] mm$^2$ | p[d] |
|---|---|---|---|---|---|---|
| rIL-6 | 7 | −1 | 6.0 ± 2.3 | 3.6 ± 1.2 | 1.8 ± 0.7 | 0.001 |
| rIL-6 | 6 | +15 | 6.7 ± 3.5 | 4.0 ± 1.9 | 1.8 ± 0.6 | 0.004 |
| PBS/10% NMS | 5 | −1 | 15.0 ± 5.6 | 3.6 ± 1.9 | 4.9 ± 1.9 | — |

[a]n = Number of mice
[b]Day of the start of twice daily treatment, where 0 is the day of virus infection.
[c]Data expressed as mean ± SD.
[d]Statistics by Student's t-test comparing the number of Ag-positive cells per mm$^2$ in the IL-6-treated mice to the number in control-treated mice.

Results. In the control-treated mice, an average of 15 virus Ag-positive cells per section was detected. This corresponded to, on average, 4.9 cells per mm$^2$ of spinal cord. In contrast, in mice receiving rIL-6, an average of 6.0 or 6.7 Ag-positive cells was detected in animals treated beginning on day −1 or day +15, respectively. This resulted, on average, in 1.8 Ag-positive cells per mm$^2$ of spinal cord. The differences in the number of Ag-positive cells per spinal cord area in rIL-6-treated mice (beginning on day −1 or day +15), compared with control-treated mice, were highly statistically significant (p=0.001 and p=0.004).

All virus Ag-positive cells at 28 days post-infection were found in the white matter. Cells could be classified into two morphologic types. Some Ag-positive cells were round with scant cytoplasm, and were present at the edge of lesions. These cells had the morphologic features of glial cells, possibly oligodendrocytes. Other Ag-positive cells were large and amorphous, with multiple intracytoplasmic vacuoles. These cells had the morphologic features of macrophages, and were usually in the midst of demyelinated lesions.

Figure 3:
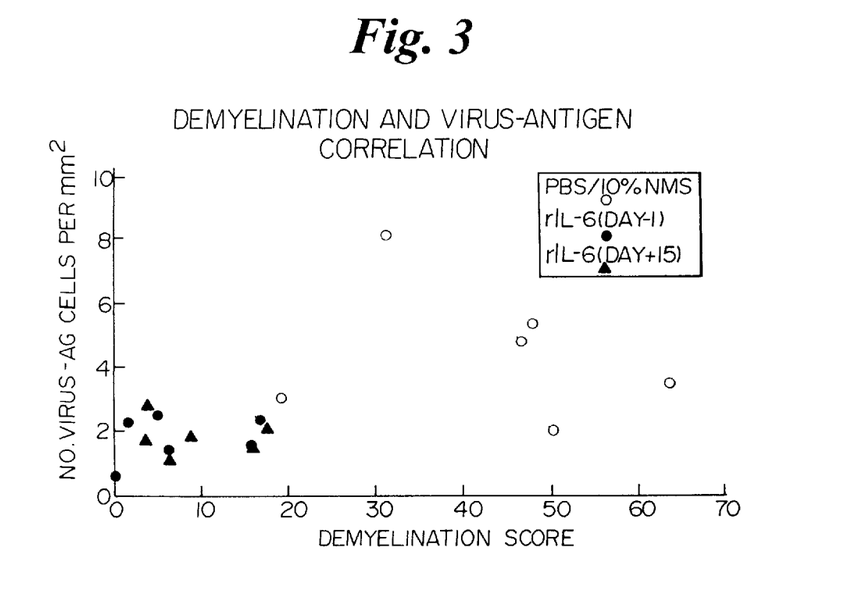
FIG. 3 is a graphic depiction of the correlation between demyelination scores and the number of virus antigen-positive cells per spinal cord area in TMEV-infected mice treated (at either day (−1) or day (+15)) and not treated with rIL-6.

For each animal, the demyelination scores obtained by erichrome staining of osmicated plastic embedded-sections were correlated with the number of virus Ag-positive cells per spinal cord area obtained by immunoperoxidase staining of frozen sections (FIG. 3). There was good correlation between these two parameters (regression p=0.017; correlation coefficient R=0.553). Animals treated with PBS/10% NMS showed the greatest demyelination scores and the most virus Ag-positive cells (FIG. 3, open circles), compared with mice treated with rIL-6 (FIG. 3, closed circles and closed triangles). This resulted in a best fit linear regression equation as follows: Number of virus Ag$^+$ cells/spinal cord area=1.632+0.052×(demyelination score).

EXAMPLE IV

Association of Demyelination with Viral Clearance

Materials and Methods. Virus Plaque Assay. Viral titers in clarified CNS homogenates were determined by plaque assay as described in Leibowitz et al., *Infect. Immun.,* 41:440 (1983) and Rodriquez et al., *Lab. Invest.,* 49:672 (1983). CNS homogenates were prepared from brains and spinal cords asceptically removed from mice killed with overdosage of ether. A 10% (w/v) homogenate was prepared in DMEM, sonicated twice for 60 seconds each time, and clarified by centrifugation. Virus preparations were stored at −70° C. before plaque assay. All plaque assays were performed in duplicate on coded samples without knowledge of treatment groups. To determine whether the suppression of demyelination observed after rIL-6 therapy was associated with virus clearance, the levels of infectious virus from the CNS of mice treated with rIL-6, compared with control mice treated with PBS/10% NMS, were determined. Mice were killed at 7, 15, 22, and 29 days after infection. Levels of infectious virus from brain and spinal cord were determined by plaque assay, expressed as $\log_{10}$ PFU per gram of CNS.

Figure 4:
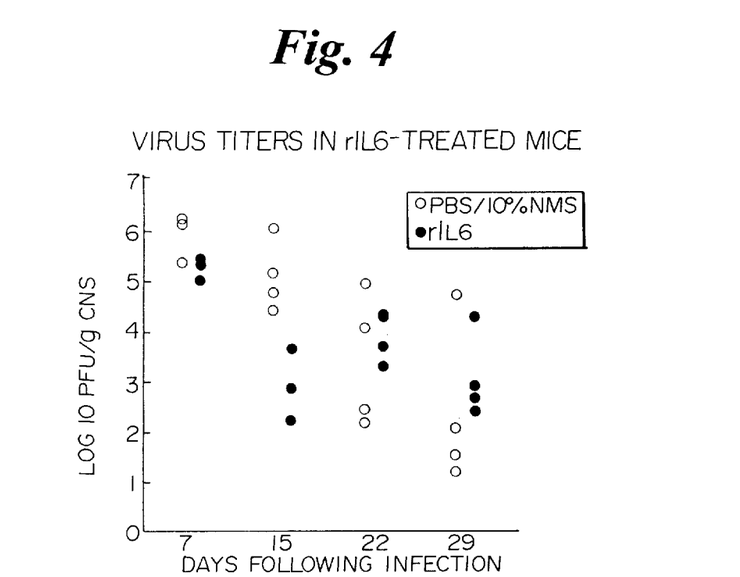
FIG. 4 is a graphic depiction of virus titers in rIL-6 or diluent-only treated TMEV-infected mice at various times following infection.

Results. On day 7 post-infection, when previous studies have demonstrated peak virus titers and acute encephalitis, no reduction in infectious virus was observed after rIL-6 therapy. In contrast, on day 15, when the virus begins to propagate from brain to spinal cord, a marked reduction in infectious virus titers was observed in rIL-6 treated mice, compared with diluent-treated mice (FIG. 4). On day 15, no overlap in the titers was observed between the treatment groups (range of 2.84 to 3.65 for rIL-6-treated mice, compared with 4.42 to 6.03 for diluent-treated mice). However, by days 22 and 29 after infection, no differences in infectious virus titers were observed between the treatment groups, such that all animals had virus persistent in CNS.

EXAMPLE V

Effect of IL-6 on Immunoglobulin Production

Materials and Methods. Total serum IgG was determined by using a capture indirect ELISA, as described in Rodriguez et al., *Microb. Pathog.,* 8:23 (1990). In summary, flat bottom Nunc-Immunoplates II were covered overnight at room temperature with rabbit anti-mouse Ig in carbonate-bicarbonate buffer (pH 9.6). Standards of purified mouse Ig were added in duplicate beginning at 20 μg/mL, followed by two-fold serial dilutions. Test sera were diluted 1/200 in PBS-Tween buffer, and then by two-fold serial dilution, and applied in triplicate. After washing, rabbit anti-mouse Ig bound to alkaline phosphatase was added, followed by Sigma Chemical Co. (St. Louis, Mo.) 104 phosphatase substrate. The reaction was stopped with sodium hydroxide after 30 minutes, and plates were read on an ELISA plate reader at a wavelength of 405 nm.

Anti-TMEV antibodies were measured by ELISAs that used purified TMEV antigen. Rodriguez et al., *Neurology,* 36:964 (1986). Sera were diluted from 1/100 to 1/100,000 in PBS buffer. Alkaline phosphotase-conjugated goat anti-mouse IgG and IgM (heavy and light chains) were used as the detecting antibody. A known hyperimmune positive control sera and several sera from uninfected mice were included in each experiment.

Titration of neutralizing antibodies was performed as described in Leibowitz et al., supra. Samples of TMEV, diluted to contain approximately 200 PFU TMEV, were mixed with an equal volume of serial twofold dilutions (1/25 through 1/800) of heat-inactivated (56° C. for 30 min) serum from TMEV-infected mice. After incubation on ice for 30 minutes, virus-serum mixtures were assayed for virus infectivity by plaque assay on L-2 cells. Neutralization titers were expressed as the $\log_2$ dilution of serum that reduced the virus plaque count by 50%.

IL-6 is known to have a potent effect on B cells and plasma cells to enhance Ig production. To determine the in vivo response of rIL-6 therapy in TMEV-infected mice, total serum Igs by ELISA was measured. TMEV-infected mice were treated twice daily with rIL-6 (beginning on day (−1) or day (+15)) or diluent PBS/10% NMS.

Figure 5:
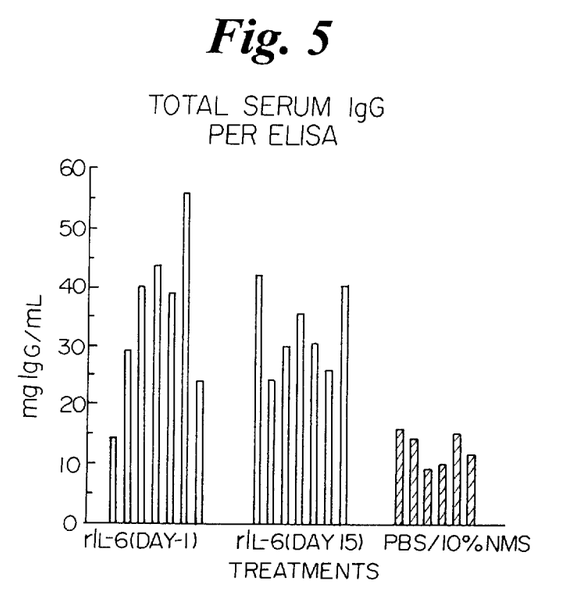
FIG. 5 is a graphic depiction of the effect of rIL-6 treatment (day (−1) and day (+15)) on immunoglobulin (Ig) production in TMEV-infected mice.

Results. rIL-6-treated mice had markedly increased serum levels of total Igs (FIG. 5). On average, diluent-treated mice had 12.6 mg Ig per milliliter of serum. In contrast, rIL-6-treated mice (combined groups beginning treatment on day −1 or day +15) had, on average, 34 mg Ig per milliliter of serum. The difference in median values between these two groups was highly statistically significant (Mann-Whitney Rank Order Sum Test, p=0.001).

Figure 6:
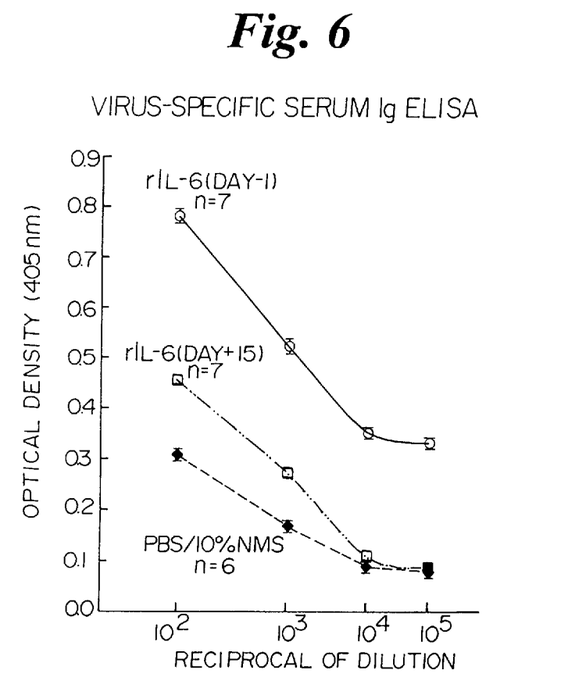
FIG. 6 is a graphic depiction of the effect of rIL-6 treatment on virus specific Ig (IgG and IgM) production in TMEV-infected mice.

Virus-specific Ig (IgG and IgM) by using ELISA to purified virus Ag was then measured. All rIL-6 treated mice, whether therapy was begun on day −1 or day +15, had higher levels of virus-specific Igs, compared with diluent-treated mice (FIG. 6). Difference in optical density at the $10^{-2}$ dilution between rIL-6-treated mice (beginning on day −1 or day +15) was highly significant statistically, compared with mice treated with PBS/10% NMS (p=0.000004 and p=0.0002, respectively). Animals treated with rIL-6 beginning on day −1 had consistently higher virus-specific Ab titers, compared with animals treated with rIL-6 beginning on day +15. This difference was statistically significant at the $10^{-2}$, $10^{-3}$, and $10^{-4}$ dilutions (all $p<0.05$).

To determine if the increased levels of anti-TMEV-specific Ab detected by ELISA reflected changes in levels of virus-specific neutralizing Ab, these sera were analyzed by a neutralizing-plaque reduction assay. Despite the higher levels of anti-TMEV-specific Ab detected by ELISA in the rIL-6-treated mice, no significant differences in mean TMEV-neutralizing Ab titers (expressed as $Log_2$) were observed among the three treatment groups: 8.38 (rIL-6, beginning on day −1); 8.09 (rIL-6, beginning on day +15); 7.00 (PBS/10% NMS beginning on day −1). Titers for the PBS/10% NMS-treated mice were, on average, only one serial dilution less than that observed in the rIL-6-treated mice.

While the foregoing examples are illustrative of the present invention, it should be recognized that other embodiments are within the scope of the appended claims and that the scope of the present invention is limited only by the following claims.

What is claimed is:

1. A method of suppressing demyelination of central nervous system tissue, comprising administering a therapeutically effective amount of interleukin-6 or an analog thereof to a mammal.

2. The method of claim 1 wherein the interleukin-6 is recombinant human interleukin-6.

3. The method of claim 1 wherein the interleukin-6 analog is an analog derived from recombinant human interleukin-6 and wherein said analog has the demyelination suppression activity of recombinant human interleukin-6.

4. The method of claim 1 wherein the interleukin-6 analog is a synthetic peptide analog of interleukin-6 and wherein said synthetic peptide analog has the demyelination suppression activity of interleukin-6.

5. The method of claim 1 wherein the step of administering a therapeutically effective amount of interleukin-6 or an analog thereof comprises parenterally administering the interleukin-6 or analog thereof.

6. The method of claim 5 wherein parenterally administering the interleukin-6 or analog thereof comprises subcutaneously administering the interleukin-6 or analog thereof.

7. The method of claim 1 wherein the step of administering a therapeutically effective amount of interleukin-6 or an analog thereof comprises enterally administering the interleukin-6 or analog thereof.

* * * * *

UNITED STATES PATENT AND TRADEMARK OFFICE
CERTIFICATE OF CORRECTION

PATENT NO. : 5,863,529
DATED : January 26, 1999
INVENTOR(S) : Moses Rodriguez

It is certified that error appears in the above-identified patent and that said Letters Patent is hereby corrected as shown below:

At Col. 1, line 52, after "role in pathogenesis", insert -- . --, and begin a new paragraph with --Of the proposed... --.

At Col. 2, line 58, please delete "IFN-9", and insert --IFN-$\beta$--.

At Col. 2, line 63, please italicize the word "Coronavirus".

At Col. 4, line 42, please italicize the word "in vivo".

Signed and Sealed this

Nineteenth Day of September, 2000

Q. TODD DICKINSON

*Attest:*

*Attesting Officer*        *Director of Patents and Trademarks*

UNITED STATES PATENT AND TRADEMARK OFFICE
CERTIFICATE OF CORRECTION

PATENT NO. : 5,863,529
DATED : January 26, 1999
INVENTOR(S) : Moses Rodriguez

It is certified that error appears in the above-identified patent and that said Letters Patent is hereby corrected as shown below:

Column 1,
Directly below the title "Suppression of Demyelination by Interleukin-6" and above the "Background of the Invention", please insert the following phrase -- This invention was made with Government Support under NS24180 awarded by the National Institutes of Health. The Government has certain rights in the invention. --

Signed and Sealed this

Sixth Day of November, 2001

Attest:

NICHOLAS P. GODICI
Attesting Officer
Acting Director of the United States Patent and Trademark Office